(12) United States Patent
Cowe (10) Patent No.: US 8,915,886 B2
(45) Date of Patent: Dec. 23, 2014

(54) AUTOINJECTOR

(75) Inventor: Toby Cowe, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 313 days.

(21) Appl. No.: 13/503,462

(22) PCT Filed: Oct. 21, 2010

(86) PCT No.: PCT/GB2010/051774
§ 371 (c)(1),
(2), (4) Date: May 22, 2012

(87) PCT Pub. No.: WO2011/048422
PCT Pub. Date: Apr. 28, 2011

(65) Prior Publication Data
US 2012/0220954 A1 Aug. 30, 2012

Related U.S. Application Data

(60) Provisional application No. 61/394,896, filed on Oct. 20, 2010.

(30) Foreign Application Priority Data

Oct. 21, 2009 (GB) .................................. 0918443.3
Oct. 14, 2010 (GB) .................................. 1017363.1

(51) Int. Cl.
*A61M 5/00* (2006.01)
*A61M 5/315* (2006.01)
*A61M 5/20* (2006.01)
*A61M 5/32* (2006.01)

(52) U.S. Cl.
CPC ....... *A61M 5/2033* (2013.01); *A61M 2005/206* (2013.01); *A61M 5/326* (2013.01); *A61M 5/3204* (2013.01); *A61M 5/31511* (2013.01); *A61M 2005/3247* (2013.01); *A61M 2005/2073* (2013.01)
USPC ......................................................... 604/187

(58) Field of Classification Search
CPC ............ A61M 5/20; A61M 2005/202; A61M 2005/206; A61M 2005/3241
USPC ......................................................... 604/187
See application file for complete search history.

(56) References Cited

U.S. PATENT DOCUMENTS 3,742,948 A 7/1973 Post et al.
5,295,965 A 3/1994 Wilmot
(Continued)

FOREIGN PATENT DOCUMENTS

FR 2 905 273 3/2008
WO 2006/129196 12/2006
(Continued)

OTHER PUBLICATIONS

Translation of Japanese Office Action, dated Apr. 8, 2014, from corresponding JP application.
(Continued)

*Primary Examiner* — Kevin C Sirmons
*Assistant Examiner* — Deanna K Hall
(74) *Attorney, Agent, or Firm* — Young & Thompson (57) ABSTRACT

An autoinjector includes a housing (10) to receive a syringe (14), and a drive mechanism including first and second springs (30, 32) operating in tandem via an intermediate member (34), on a plunger (42). The plunger is retained in a locked position by a trigger. Release of the trigger causes the first spring to advance the syringe to an arrest point whereafter the second spring extends within the syringe to expel a dose.

17 Claims, 13 Drawing Sheets

(56) References Cited

U.S. PATENT DOCUMENTS

| | | |
|---|---|---|
| 7,976,514 B2 | 7/2011 | Abry et al. |
| 2008/0009807 A1 | 1/2008 | Hommann |

FOREIGN PATENT DOCUMENTS

| | | |
|---|---|---|
| WO | 2008029280 A2 | 3/2008 |
| WO | 2009/007229 | 1/2009 |
| WO | 2009/063030 | 5/2009 |

OTHER PUBLICATIONS

International Search Report dated Jul. 29, 2011, corresponding to PCT/GB2010/051774.

British Search Report dated Feb. 10, 2010, corresponding to the Foreign Priority Application No. GB 0918443.3.

AUTOINJECTOR

This invention relates to autoinjectors.

There is a need for autoinjectors which are of compact form so that they can be carried and used unobtrusively and further which are simple to manufacture, assemble and use with consequent savings in manufacturing and assembly costs, and a lower environmental impact.

Accordingly, in one aspect, this invention provides an autoinjector for receiving in use a syringe containing a dose of medicament, said syringe comprising a syringe body of generally cylindrical form, a needle at the forward end of the syringe body, and a piston slideably mounted in said syringe body for expressing a dose, said autoinjector comprising:
- a housing for receiving in use said syringe for sliding movement between a retracted position and an extended, injection position in which said needle projects from said housing;
- a drive mechanism for being released from an energised condition to drive the syringe forwards to the injection position and to expel a dose;
- wherein said drive mechanism includes:
- a plunger adapted to drive said piston in use;
- an intermediate drive member;
- a first compression drive spring disposed between said intermediate drive member and said housing or a part associated therewith to urge said intermediate drive member forwardly, and
- a second compression spring acting between said intermediate drive member and said plunger to urge said plunger forwardly,
- the intermediate drive member having an internal cylindrical space for receiving the rear end of said second compression spring, whereby following release of said drive mechanism, the second spring, as it expands, is surrounded along at least a major portion of its length by at least one of the cylindrical space and the internal bore of the syringe body.

In this arrangement, the external support provided to the second compression spring means that a long spring of relatively narrow diameter may be used without the risk of snaking or the need to provide an internal support along its length. In turn, the ability to use a relatively low diameter spring means that in preferred embodiments, the spring can be designed to fit into the interior of the syringe body rather than expanding exteriorly, and this means that the overall length of the device may be reduced as less of the expansion takes place outside the syringe, thereby providing a compact design. It will be appreciated that the second spring could act directly on the piston if the latter is suitably formed.

Preferably the intermediate member comprises a generally cylindrical body, closed at its rear end. In this fashion, the intermediate member provides an internal cylindrical wall surface for externally constraining at least part of the second spring, and an external cylindrical surface for internally constraining at least part of the first spring.

Conveniently, the autoinjector is configured so that, upon release of the drive mechanism, the intermediate member is urged close to or in contact with the rear end of the syringe, thereby substantially completely to enclose the second spring to constrain it externally. Preferably, the drive mechanism includes a trigger arrangement adapted releasably to prevent movement of the intermediate member from a cocked position. The trigger arrangement preferably includes a latch member engageable with an abutment surface on said intermediate member. The abutment surface preferably is disposed between the forward end of the intermediate member and the rearward end of the syringe when in said cocked position. Preferably, the trigger arrangement is released by a trigger element, which may be biased away from its release position by one or both of the drive springs. It is common in autoinjectors to provide a small spring to provide a bias or controlled resistance to the firing button, and to prevent free motion or rattling. By using the drive spring to supply a bias, an extra spring is not required for this purpose. This is a significant benefit in automatically assembled devices, where spring handling and detangling can be problematic.

Many existing autoinjectors require some system of mechanical sequencing or latch to sequence the syringe advance movement and the syringe plunger movement of the autoinjector. Such mechanisms add to the complexity of the autoinjector and also contribute to its length. Accordingly, we have designed a compact autoinjector which does not require such mechanisms and in which, immediately on release of the drive mechanism, the plunger and the intermediate member are free for relative movement. In the conventional mechanisms described above, the intermediate member and the plunger continue to be actively locked against movement until they have reached a forward position, where they are unlatched.

Accordingly, in another aspect, this invention provides an autoinjector for receiving in use a syringe containing a dose of medicament, said syringe comprising a syringe body of generally cylindrical form, a needle at the forward end of the syringe body, and a piston slideably mounted in said syringe body for expressing a dose, said autoinjector comprising:
- a housing for receiving in use said syringe for sliding movement between a retracted position and an extended, injection position in which said needle projects from said housing;
- a drive mechanism for being released from an energised condition to drive the syringe forwards to the injection position and to expel a dose;
- wherein said drive mechanism includes:
- a plunger adapted to drive said piston in use;
- an intermediate drive member;
- a first compression drive spring disposed between said intermediate drive member and said housing or a part associated therewith to urge said intermediate drive member forwardly, and
- a second compression spring acting between said intermediate drive member and said plunger to urge said plunger forwardly,
- wherein immediately on release of said drive mechanism said intermediate drive member and said plunger are freed for relative movement.

In yet another aspect there is provided an autoinjector for receiving in use a syringe containing a dose of medicament, said syringe comprising a syringe body of generally cylindrical form, a needle at the forward end of the syringe body, and a piston slideably mounted in said syringe body for expressing a dose,
said autoinjector comprising:
- a housing for receiving in use said syringe for sliding movement between a retracted position and an extended, injection position in which said needle projects from said housing;
- a drive mechanism being released from an energised condition to drive the syringe forwards to the injection position and to expel a dose;
- wherein said drive mechanism includes:
- a plunger adapted to drive said piston in use;
- an intermediate drive member;

a first compression drive spring disposed between said intermediate drive member and said housing or a part associated therewith to urge said intermediate drive member forwardly, and a second compression spring acting between said intermediate drive member and said plunger to urge said plunger forwardly, wherein the second spring is selected such that the spring force it exerts when substantially fully compressed is less than the force required to overcome the static friction between the piston and the syringe body, but greater than the force required to maintain movement of the piston once the static friction has been overcome by the residual force in the first spring when the syringe is in its injection position.

Whilst the invention has been described above, it extends to any inventive combination feature disclosed in the description or drawings.

The invention may be performed in various ways and several embodiments thereof will now be described in detail, by way of example only, reference being made to the accompanying drawings, in which.

Figure 1:
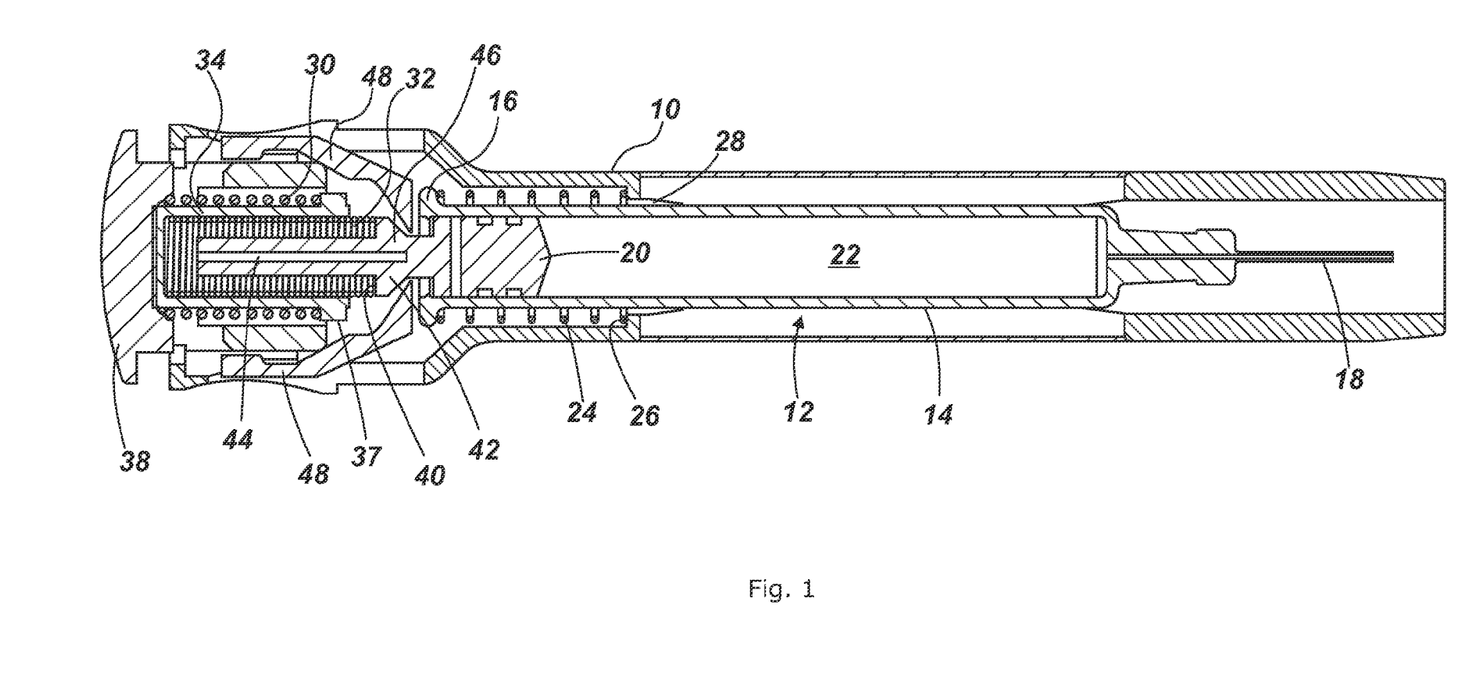
FIG. 1 is a section view of a first embodiment of autoinjector of this invention in a pre-use cocked position.

Referring initially to FIG. 1, the autoinjector comprises an outer housing 10 of cylindrical form in the bore of which is slideably located a syringe 12. The syringe 12 is of generally conventional form comprising a syringe body 14 having a flange 16 at its rear end with a needle 18 projecting from the front end. A piston 20 is slideably contained in the syringe body for expulsion of a medicament 22. The syringe 12 can slide in the housing from a rearward position as shown in FIG. 1, against a bias provided by a compression spring 24, to a forward position defined by an internal shoulder 26 on the housing and the compressed spring 24, in which the needle 18 projects from the housing. The syringe is centrally located in the housing by a rib 28 on the body.

Figure 2:
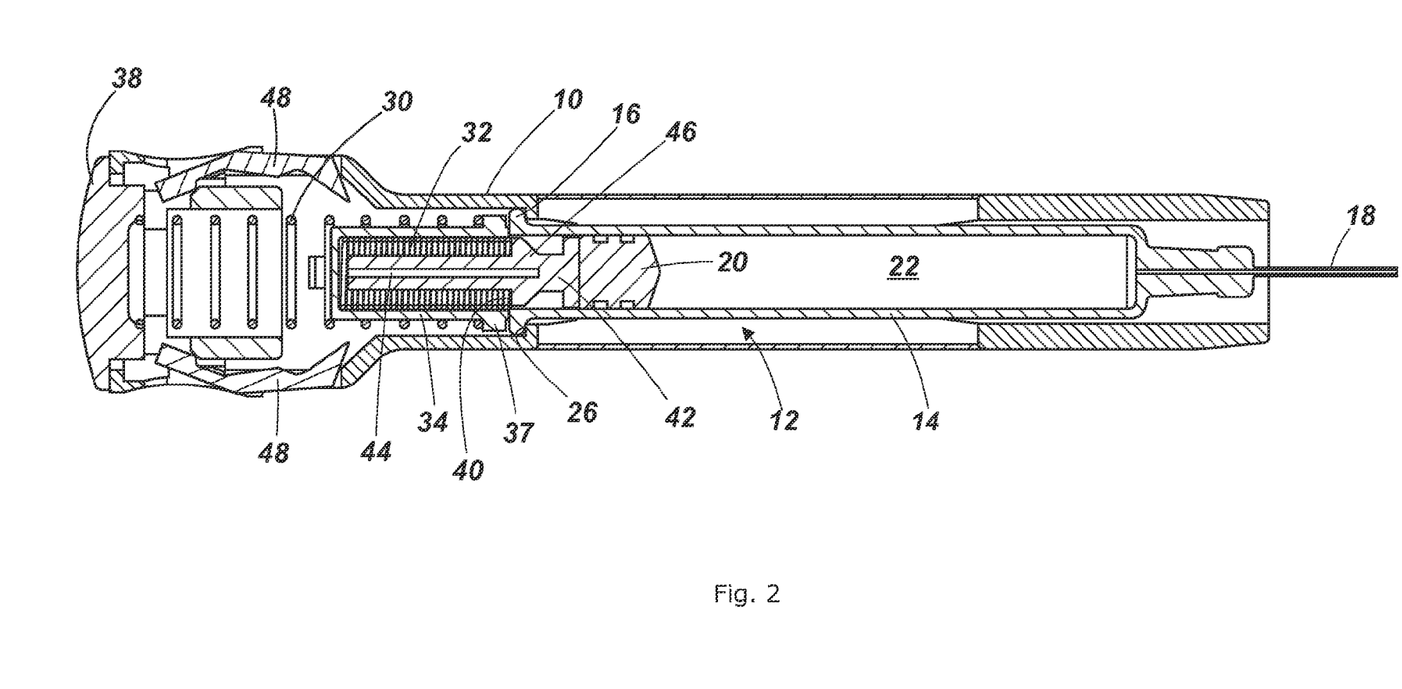
FIG. 2 is a section view of the embodiment of FIG. 1, with the trigger button depressed and the syringe moved forwardly ready to deliver a dose.
Figure 3:
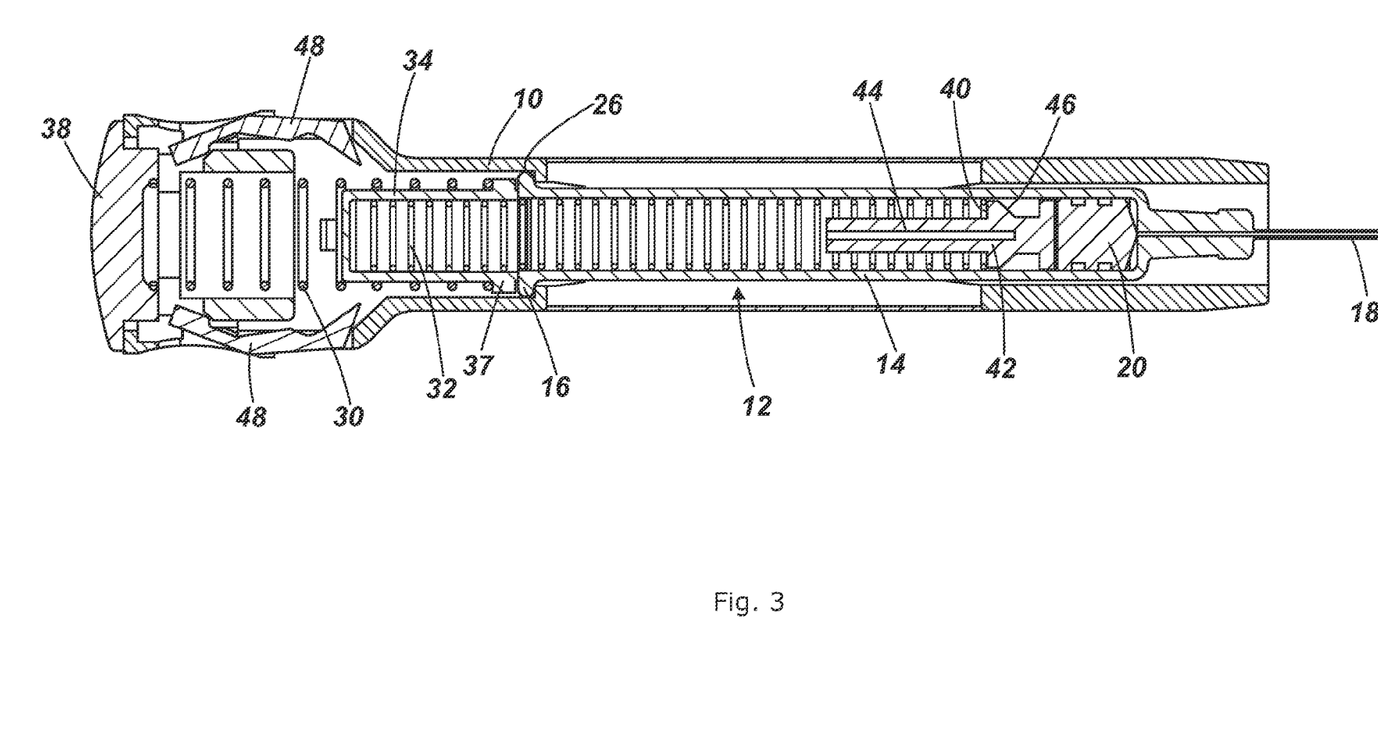
FIG. 3 is a section view of the embodiment of FIGS. 1 and 2, following expulsion of a dose.
Figure 4:
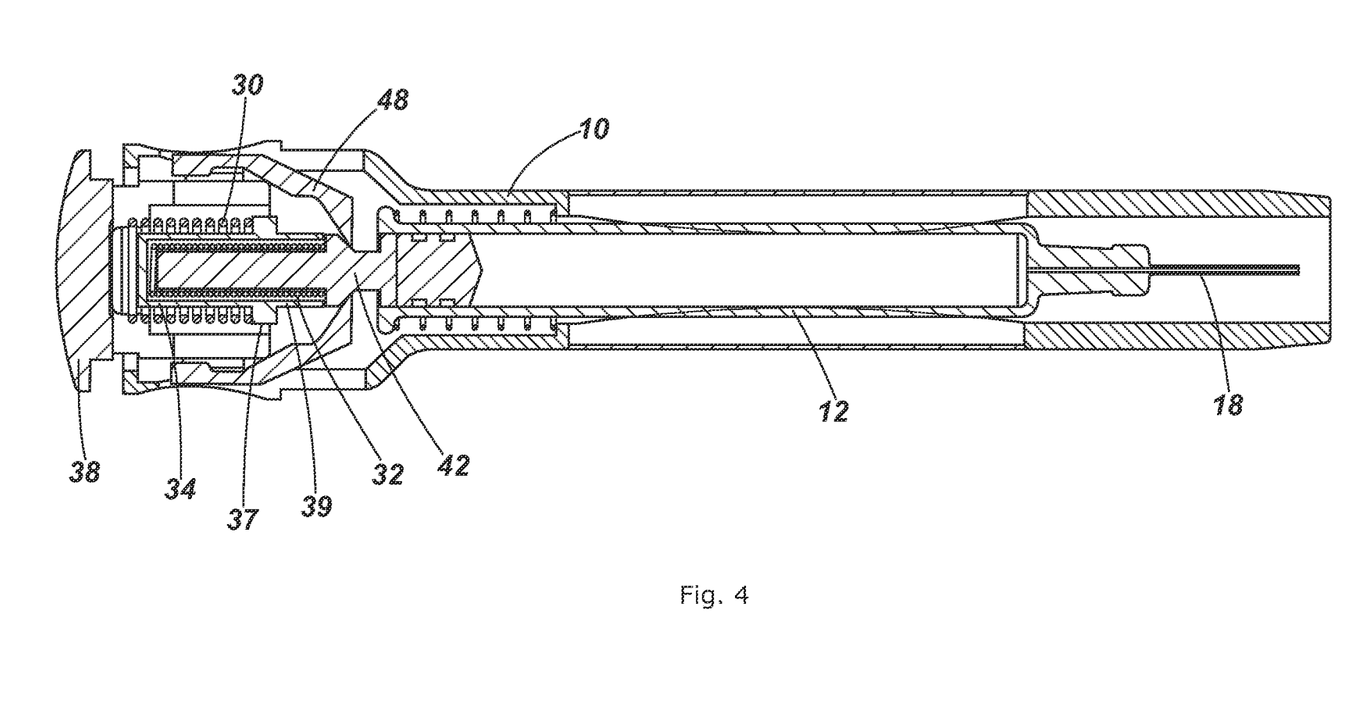
FIGS. 4 to 7 are section views of a second embodiment of autoinjector.
Figure 5:
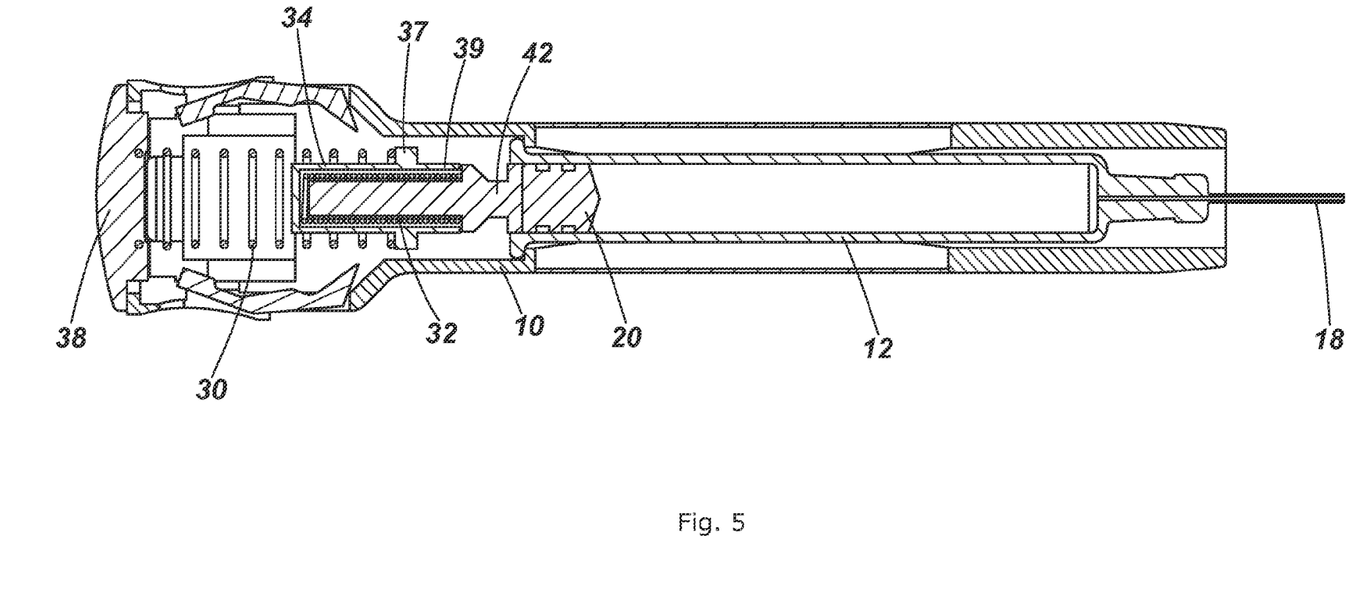
Figure 6:
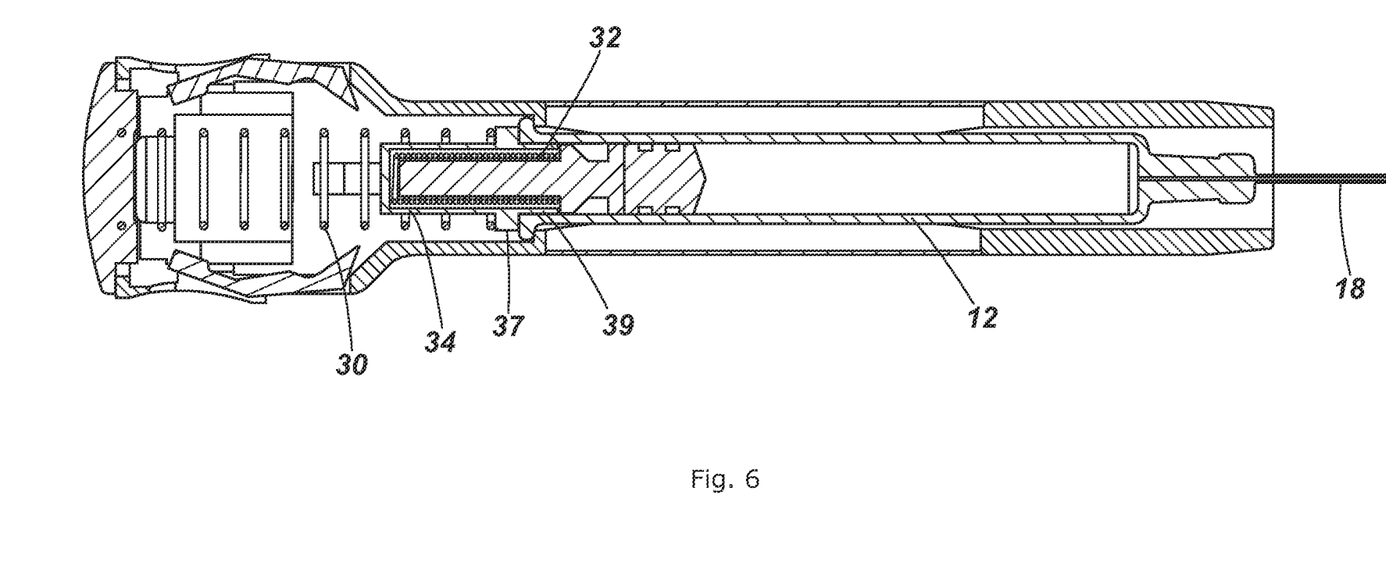
Figure 7:
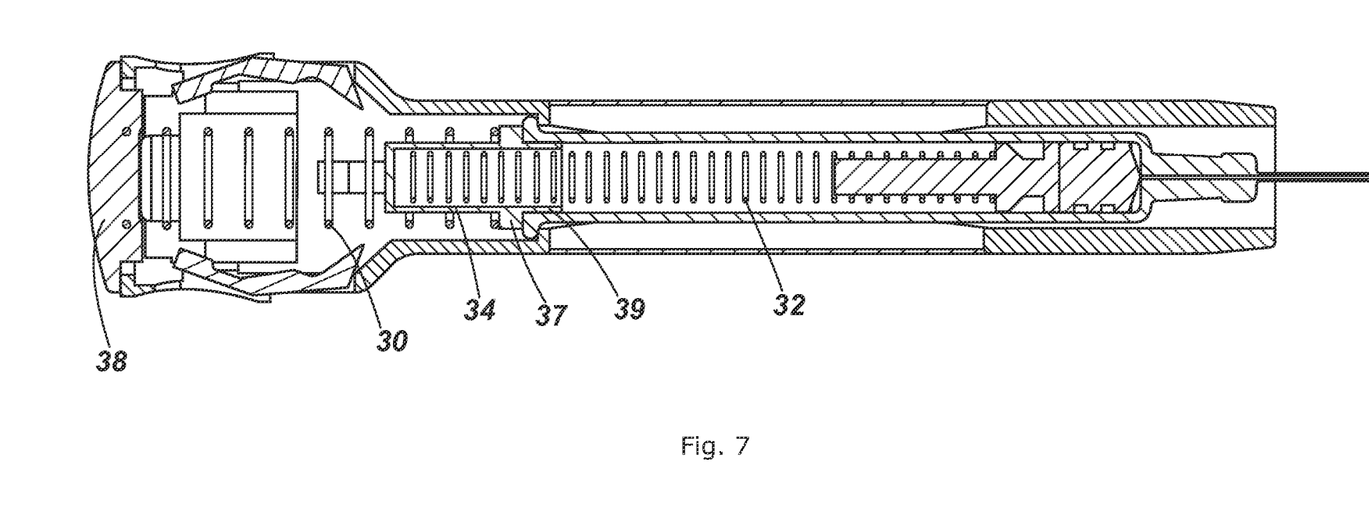
Figures 8, 9:
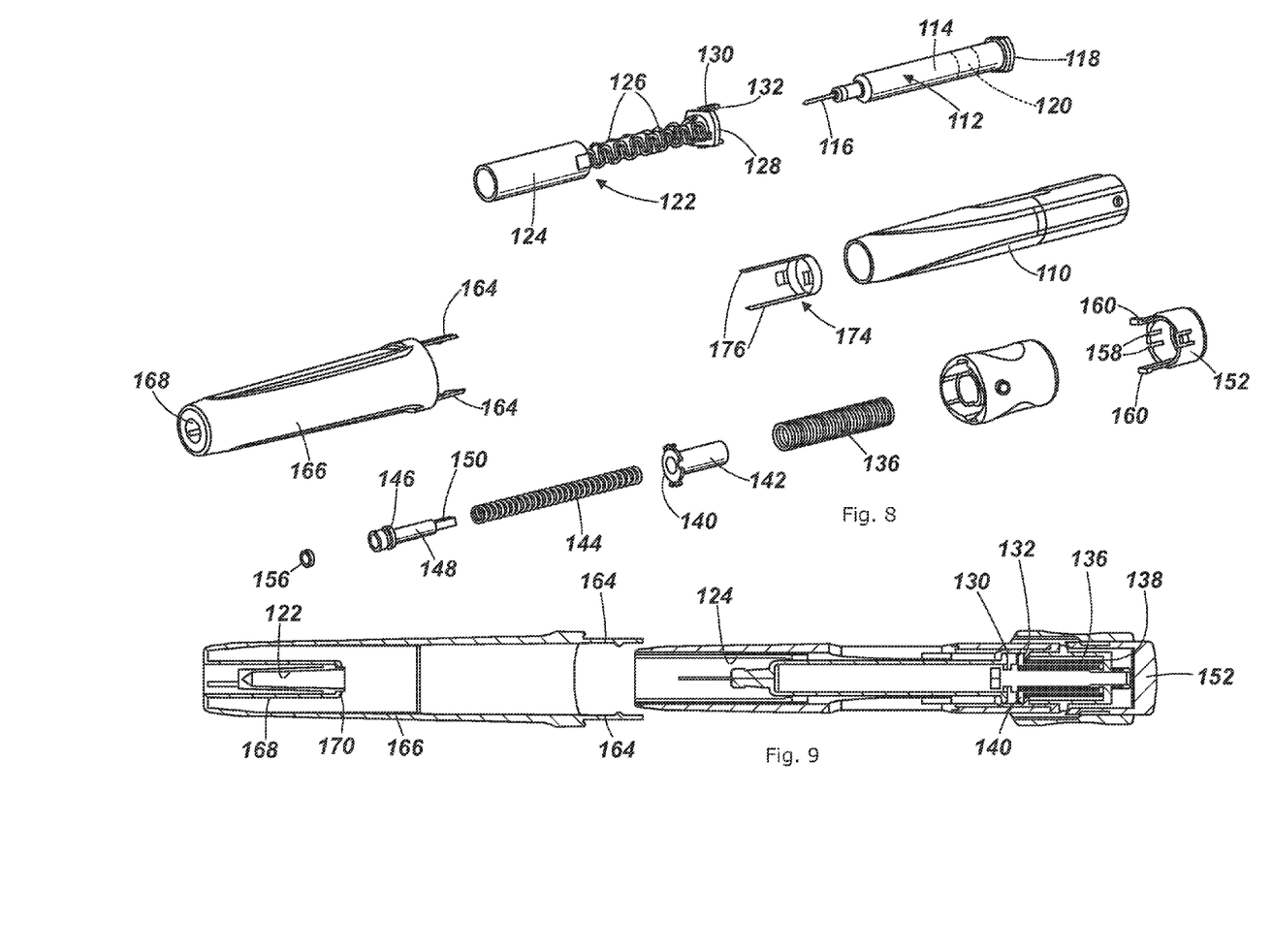
FIG. 8 is an exploded view of a third embodiment of an autoinjector in accordance with this invention.
FIG. 9 is a side section view through the autoinjector of FIG. 8 assembled and prior to use.
Figure 10A:
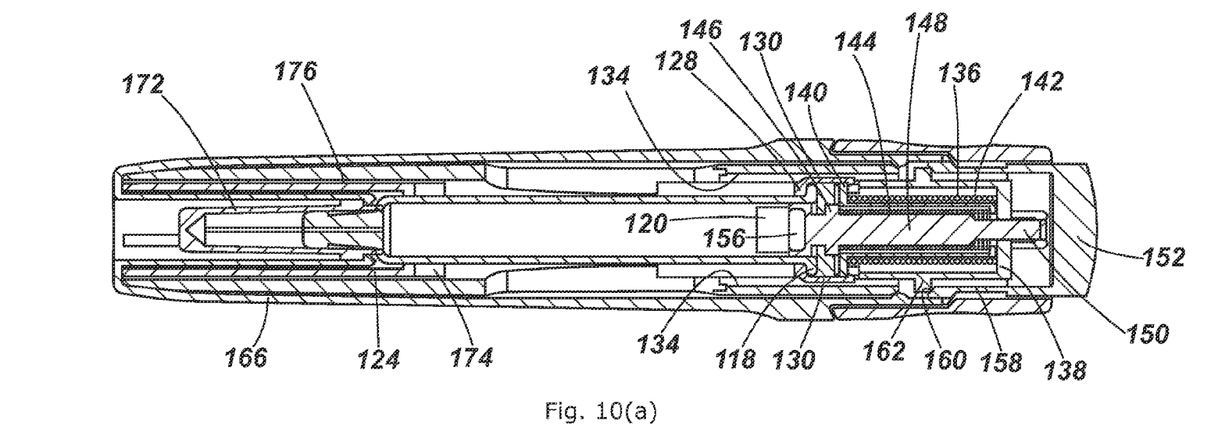
FIGS. 10(a) and (b) are respective side and top section views of the autoinjector with the cap in place, and removed.
Figure 10B:
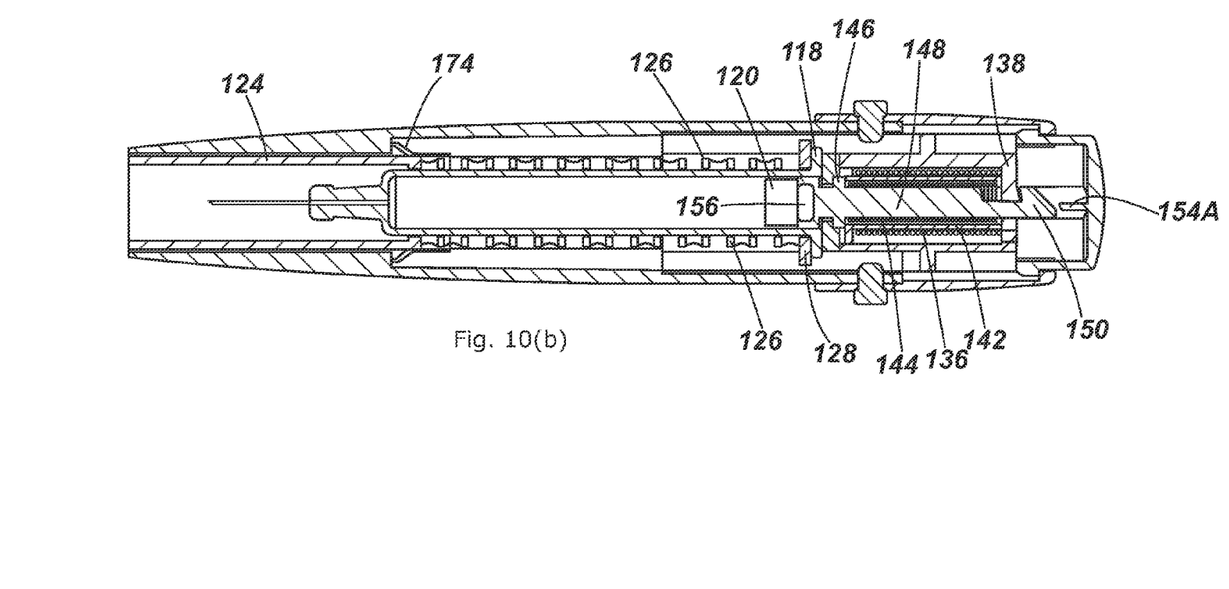
Figure 11A:
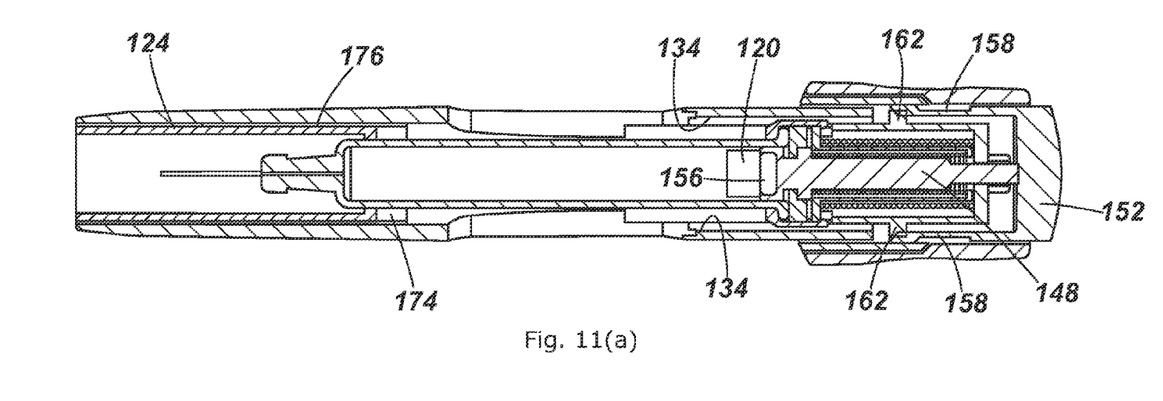
FIGS. 11(a) and (b) are respective side and top section views of the autoinjector with the firing button partially depressed immediately prior to the release of the plunger.
Figure 11B:
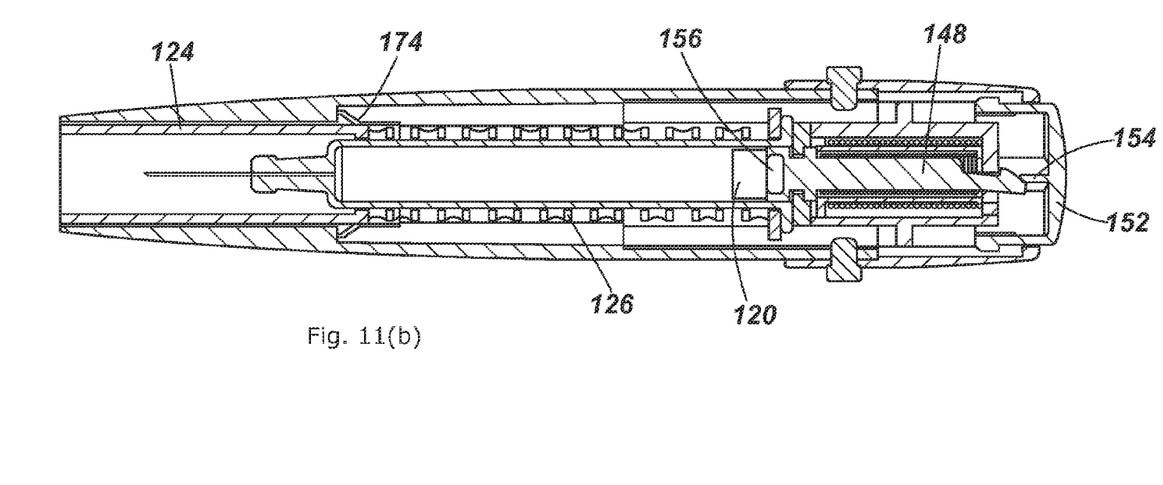

In the rear end of the housing 10 is provided a drive mechanism for the autoinjector. This comprises first and second compression springs 30, 32 that act in tandem via an intermediate member 34 on a plunger member 42. At its rear end, the first spring 30 is anchored in an internal bore of a trigger button 38, which is captive to the housing. The trigger button may be moved from the rearward position shown in FIG. 1 to the forward position shown in FIGS. 2 and 3 to fire the device as to be described below. The forward end of the first spring 30 surrounds the closed rear end of the intermediate member 34 and abuts a collar 37 on the outside thereof. The rear end of the second spring 32 engages the inner closed rear end of the intermediate member 34 and is externally constrained thereby. The front end of the second spring abuts a shoulder 40 on a plunger 42 which has a rear stem 44 that fits within the compressed second spring as shown in FIGS. 1 and 2.

The plunger 42 has a frustoconical latch surface 46 which is latched by a pair of latch fingers 48 pivoted on the housing 10. The latch fingers 48 are constrained against pivoting movement when the trigger button 38 is in its rear position as shown in FIG. 1, but splay outwards to release the plunger 42 when the trigger button is pushed to its forward position. The trigger button has apertures into which the rear ends of the latch fingers 48 can pivot when the button is pushed forwardly.

In use, from the position shown in FIG. 1, the autoinjector is offered up to the injection site with the front end in contact with the skin. After removing any safety catch, the trigger button 38 is pressed in against a bias afforded by the first spring 30 so that the latch fingers pivot to release the plunger 42 and intermediate member 34 for forward movement. The first spring 30 is stronger than the second spring 32 and so, initially, the intermediate member 34 plunger 42, piston 20, and syringe 14 move as one under the influence of the first spring to drive the syringe to its forward position to extend the needle. During this phase, the reaction or resistance to the forward movement of the syringe as the syringe moves forwardly in the housing and the needle penetrates the flesh is relatively low and less than the break out force required to advance the piston down the syringe. Having reached its forward position, the syringe is arrested, and continued expansion of the first spring pushes the intermediate member 34 towards the now stationary syringe until the collar 37 of the intermediate member is butted up against the rear end of the syringe (FIG. 2). As this occurs the intermediate member 34 initially closes towards the plunger 42, slightly further compressing the second spring 32, until the second spring is fully compressed, whereupon the intermediate member 34, the plunger 42 and piston 20 shift forwards relative to the syringe so that, following arrest of the syringe, the more powerful thrust of the first spring 30 is utilised to overcome the static friction or break out force between the piston and the syringe body. Thereafter, the second spring 32 urges the piston forwards to expel a dose, whilst the intermediate member remains butted up against the rear of the syringe. During this latter phase of operation, the second spring is wholly externally enclosed in the internal space defined between the syringe and the intermediate member. In addition, the harnessing of the power of the first spring 30 to overcome the static friction between the piston and the syringe means that the second spring can be less powerful as it only needs to provide a glide force and to pressurise the medicament to exit the needle.

Turning now to the second embodiment illustrated in FIGS. 4 to 7, this is similar in many respects to the first embodiment and like parts are given like references. The main difference is in the design of the intermediate member 34. In the second embodiment the intermediate member has a further cylindrical shell section 39 that extends forwardly of the collar 37 and can enter the rear end of the syringe. In this embodiment the cylindrical shell section offers fully enclosed support of the second spring 32 until it expands with the body of the syringe. Without such a shell a forward portion of the spring is exposed in the initial stages, but equally in this case the second spring diameter can be increased to approximately the inner diameter of the syringe, which can be advantageous.

Referring now to FIGS. 8 to 11, the third embodiment of autoinjector comprises an outer housing 110 of cylindrical form in the bore of which is disposed a syringe 112 of known form with a barrel 114, a needle 116 extending from the forward end, and a flange 118 at its rear end. A medicament is contained within the syringe and can be expressed through the needle by a piston 120 inside the barrel. The syringe is supported and surrounded by moulded plastics shroud/carrier 122 assembly comprising a forward hollow cylindrical portion 124 integrally formed with diametrically opposed springs 126 to either side, and a collar 128 adapted to engage the forward face of the syringe flange. Extending rearwardly from the collar are two diametrically opposed clearance fingers 130 with barbed teeth 132 that engage the intermediate member, to ensure that the collar 128 and thus the syringe 112 cannot separate by more than a short distance from the intermediate member 142 described below when the needle shield is pulled off the syringe prior to injection. The barbed teeth 132 run in respective diametrically opposed grooves 134 on the inner surface of the rear part of the housing. In the pre-use position, the shroud portion 124 is telescopically received within the forward end of the housing and coterminous therewith.

In the rear of the housing is provided a drive mechanism which comprises a first outer spring 136 which acts between the front face of a transverse inner wall 138 at the rear of the housing and a forward flange 140 of a top hat-shaped intermediate member 142. An inner, second, spring 144 is received within a cylindrical part of the intermediate member 142 and acts between an inner face of the rear end wall thereof and a circumferential rib 146 on the forward part of a plunger 148. At the rear end, the plunger has a resilient hooked arm 150 (see FIGS. 8, 11(b)) which latches around the edge of an aperture in the transverse inner wall 138 of the housing. Projecting rearwardly from the rear end of the housing is a captive axially slideable trigger button 152 movable against a rearward bias from the position shown in e.g. FIG. 11(a), where a release finger 154 is spaced rearwardly of the hooked arm 150, to a forward position (FIG. 11(b)) where the finger 154 cams the hooked arm to release its retention by the wall 138, thereby allowing the springs 136, 144 to drive the plunger 148 forwardly. The plunger is shaped and sized so that it can pass into and down the internal bore of the syringe barrel 114, to urge the piston 120 to express a dose. In the forward end of the plunger is a cylindrical recess in which is located a small powerful magnet 156.

The trigger button 152 is biased rearwardly by means of two integral forwardly extending sprung arms 158 with cam surfaces 160 which ride over respective abutments 162 inside the rear of the housing. However, initially, forward movement of the trigger button is prevented by means of two rearwardly extending locking arms 164 which extend back from the rear end of a cap 166. The cap covers the whole of the forward end of the housing and has a re-entrant cylindrical portion 168 with claw features 170. The claw features 170 slip over the rear end of a needle shield 172 which is secured to the front end of the needle during manufacture. Thus the cap 166 fulfils the functions of acting as a safety catch for the trigger button 152, serving as a shield remover.

Anchored inside the forward end of the housing is a latch 174 formed of pressed steel or other ferro-magnetic material to provide two latch arms 176 which extend forwardly from an anchorage normally to sit in an annular space between the shroud 124 and an inner part of the housing wall.

Figure 12A:
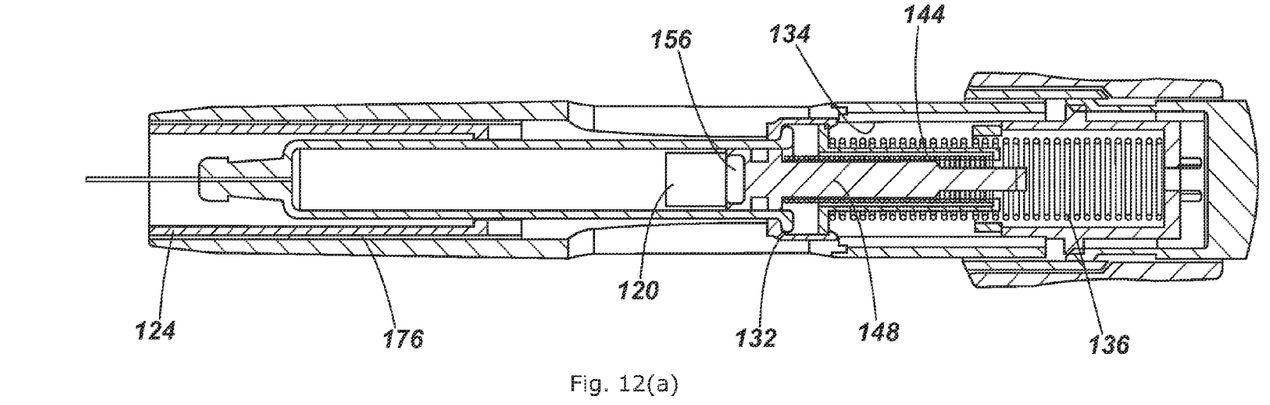
FIGS. 12(a), (b) and (c) are respective side section views showing the autoinjector with the syringe in its forwardmost position, shortly after breakout of the piston, and at the injection complete stage respectively.
Figure 12B:
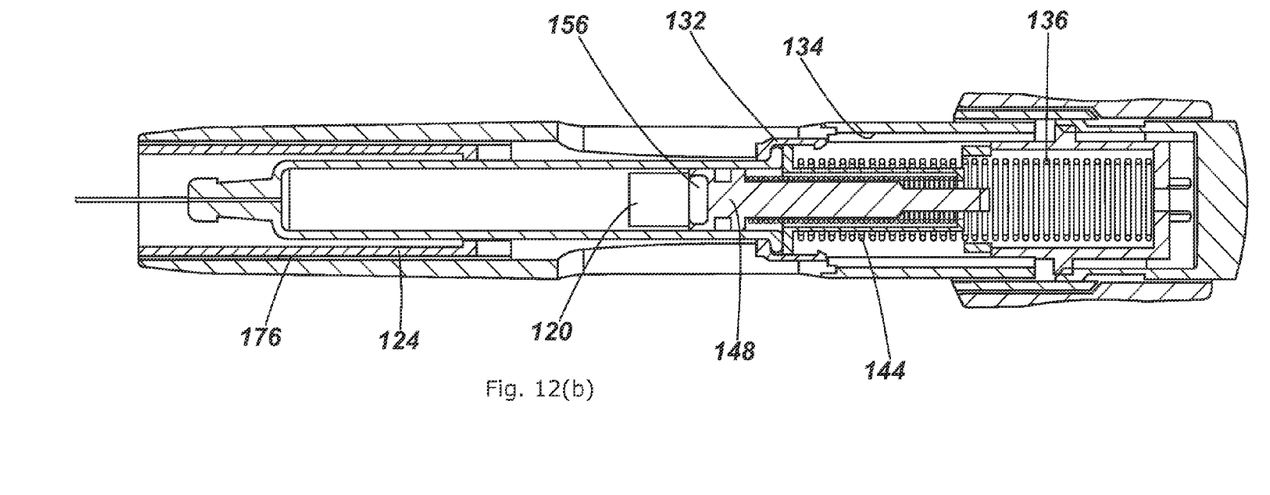
Figure 13:
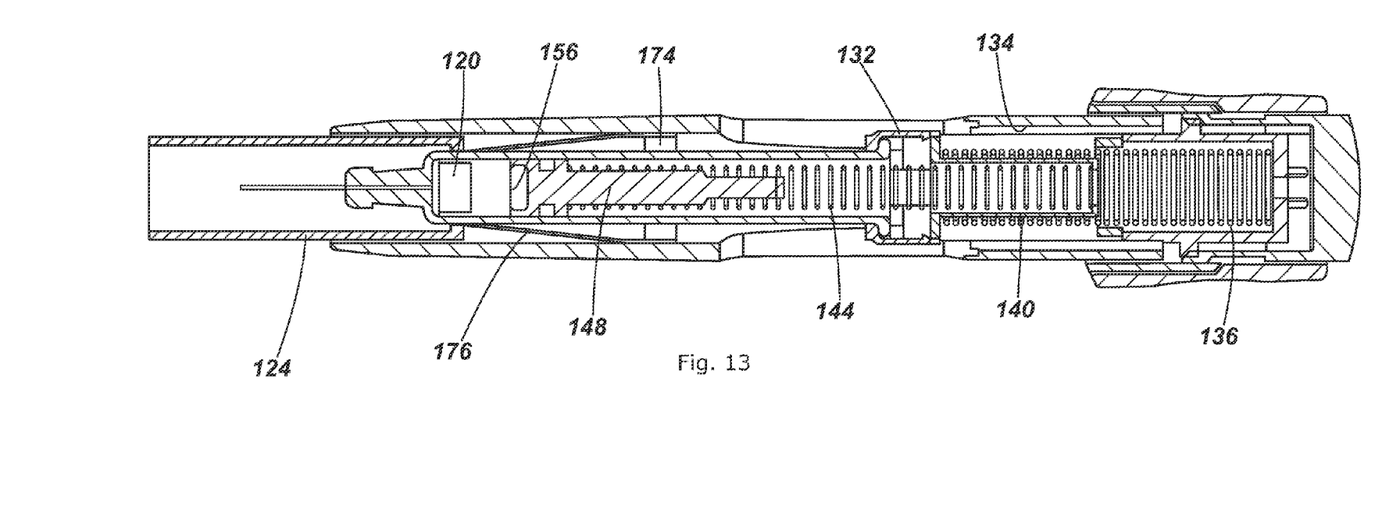
FIG. 13 is a view of the device after use, with the shroud extended and locked out by the magnetically enabled latch.

In operation, the user pulls the cap 66 off forwardly which removes the needle shield 122 from the syringe and arms the device by rendering the trigger button 152 operational. The user then offers the injection device up to the injection site and presses the trigger button 152. This releases the hooked arm 150 of the plunger 148 as shown more particularly in FIG. 12(b). Once the plunger is released, the first spring 136 expands to extend the syringe 120 so that the needle penetrates the flesh. During this period (FIG. 13(a)), the second spring 144 remains substantially fully compressed, with the plunger 148 bearing against the piston 210 within the syringe but not moving it relative to the syringe, so that the thrust of the first spring is transmitted via the intermediate member 142, the compressed second spring and the piston to the syringe.

Figure 12C:
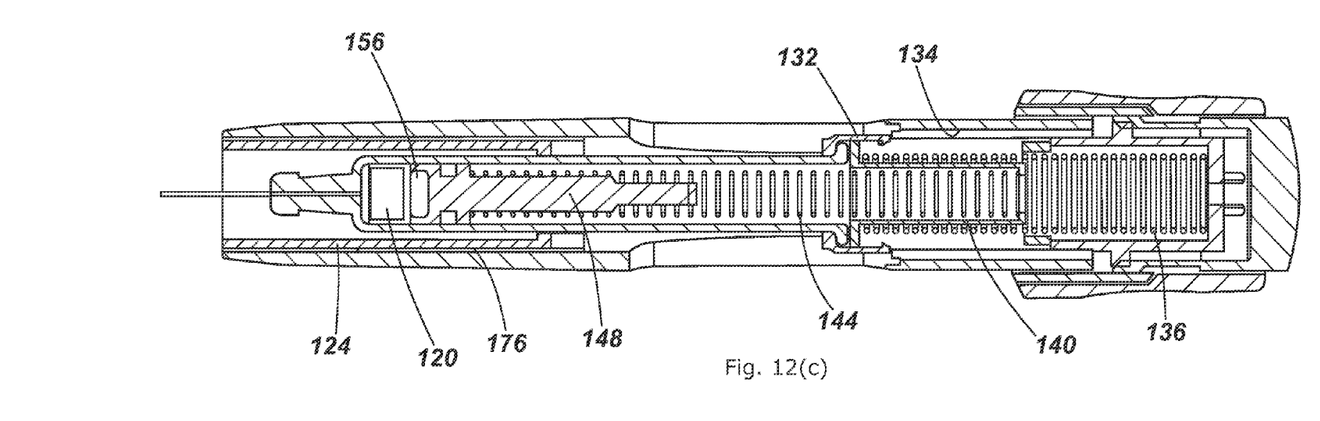

At its extended position, the syringe is arrested by the compression spring portions 126 bottoming out, the shroud 124 being held against movement by contact with the skin surface. When the syringe is arrested, the first spring 136 continues to expand to drive the flange 140 of the intermediate member into engagement with the syringe flange 118 thereby contributing to the force required to initiate movement of the piston down the syringe (FIG. 12(b)). From this position the second spring 144 expands to drive the piston down the barrel of the syringe to express a dose. At the end of its travel, it will be noted that the magnet 156 in the plunger is spaced between the latching arms 176 of the latch 174, as shown in FIG. 12(c). When the dose has been expressed, the user pulls the device away from the flesh and so the shroud portion 124 is free to expand under the influence of the compression spring portions 126. The shroud portion is driven by the springs 126 forwardly beyond the front tips of the latching arms 176. Once this happens, the latching arms are free to move inwardly to the latching positions shown in FIG. 13, under the influence of the magnet 120. The shroud portion 124 is therefore locked out and the device thereby rendered safe.

In other embodiments, not shown, further magnets or ferro-magnetic material may be disposed in the front end of the housing around or in front of the syringe in order to provide a magnetic boost effect as the plunger nears the end of its stroke.

Figure 14:
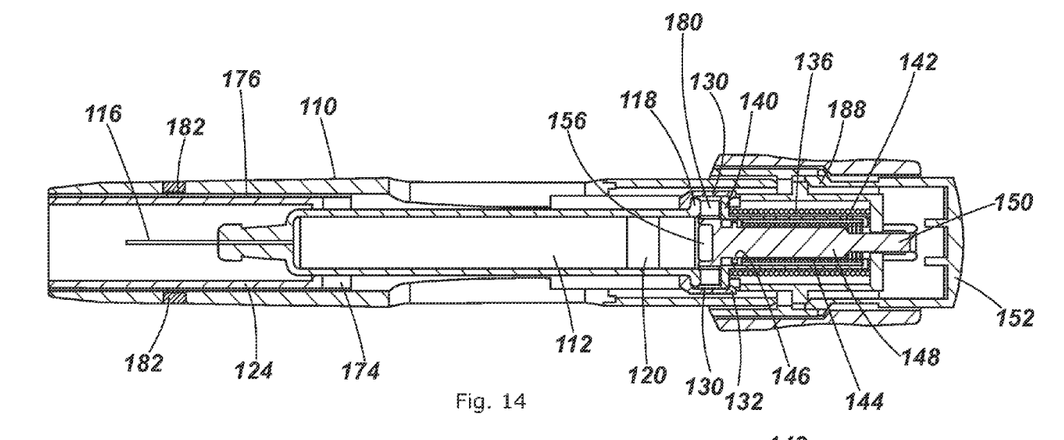
FIG. 14 is a side view through a fourth embodiment of an autoinjector.
Figure 15:
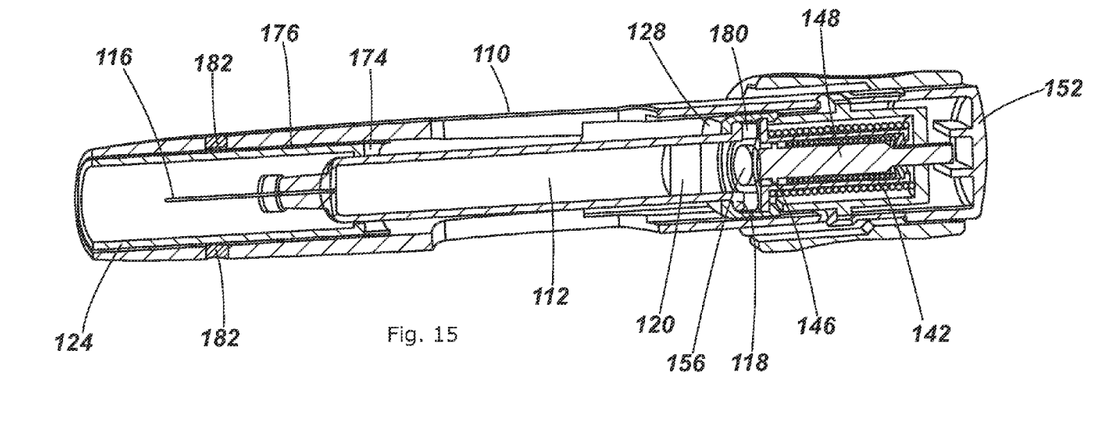
FIG. 15 is a shaded side view of the fourth embodiment.

Referring now to FIGS. 14 and 15 the fourth embodiment has many of the same components as the third embodiment and which act in a similar fashion. These components are given the same reference numbers and will not therefore be described in detail again. This second embodiment incorporates a magnetic coupling embodiment between the plunger 148 and the syringe designed so that during an initial penetration phase of movement the plunger is coupled magnetically to a thrust collar 180 of ferro-magnetic material that is positioned in contact with the rear face of the syringe flange 118. Thus the plunger 148 and the syringe 118 are initially held against relative movement and so move as one during this phase, until the syringe is arrested by reaching its forwardmost position, with the needle inserted into the injection site. Upon arrest of the syringe, the spring force acting on the plunger overcomes the magnetic coupling force and the coupling yields so that the plunger is released to move forward relative to the syringe to move the plunger into contact with and to urge the piston forwardly to expel a dose. As previously, as the plunger moves alongside the ferro-magnetic latching arms 176 and they are attracted inwardly. This is enhanced in the embodiment by provision of two magnets 182 on the forward ends of the latching arms. These magnets are aligned so as to be attached towards and to exert a pull on the magnet 156 in the plunger to provide a magnetically influenced forward boost to the plunger toward the forwardmost end of its stroke. Upon completion of the injection and removal of the device from the site, the shroud 124 extends forwardly as the spring portions 126 re-expand, and as a rearward lip on the shroud passes the magnets, the latching arms move inwards to block retraction movement of the shroud and thereby lock it out. The magnets 182 may be housed slideably in through-holes in the housing wall, allowing them also to move inwards with the latching arms as the rearward lip on the shroud passes the magnets, and so provide a visual and tactile confirmation of locking out of the shroud 124.

In either of the embodiments incorporating magnetic latching, the latches may be arranged that they, or a component associated therewith, emits an audible click as the mechanism latches, thereby to confirm that the injection is complete.

The invention claimed is:

1. An autoinjector for receiving in use a syringe containing a dose of medicament, said syringe (12) comprising a syringe body (14) of generally cylindrical form, a needle (18) at the forward end of the syringe body, and a piston (20) slideably mounted in said syringe body for expressing a dose,
    said autoinjector comprising:
        a housing (10) for receiving in use said syringe (12) for sliding movement between a retracted position and an extended, injection position in which said needle (18) projects from said housing;
        a drive mechanism (30-36) for being released from an energised condition to drive the syringe forwards to the injection position and to expel a dose;
    wherein said drive mechanism includes:
        a plunger (36) adapted to drive said piston (20) in use;
        an intermediate drive member (34);
        a first compression drive spring (30) disposed between said intermediate drive member and said housing or a part associated therewith to urge said intermediate drive member forwardly (34), and
        a second compression spring (32) acting between said intermediate drive member and said plunger to urge said plunger (36) forwardly,
        the intermediate drive member (34) having an internal cylindrical space for receiving the rear end of said second compression spring (32), whereby following release of said drive mechanism, as it expands the second spring is surrounded along at least a major portion of its length by at least one of the cylindrical space and the internal bore of the syringe body.

2. An autoinjector according to claim 1, wherein the intermediate drive member (34) comprises a generally cylindrical body providing an internal cylindrical support surface for externally constraining the second spring and an external cylindrical surface for internally constraining the first spring.

3. An autoinjector according to claim 1, wherein said first spring (30) is stronger than said second spring (36) and selected such that said second spring (32) remains substantially compressed at least until the syringe has reached its injection position.

4. An autoinjector according to claim 2, wherein the second spring (32) is selected such that the spring force it exerts when substantially fully compressed is less than the force required to overcome the static friction between the piston (20) and the syringe body (14), but greater than the force required to maintain movement of the piston (20) once the static friction has been overcome by the residual force in the first spring when the syringe is in its injection position.

5. An autoinjector according to claim 1, wherein upon release of said drive mechanism, said intermediate member (34) is urged close to or in contact with the rear end of the syringe, thereby substantially completely to enclose the second spring to constrain it externally.

6. An autoinjector according to claim 1, including a trigger arrangement (38, 48) adapted releasably to prevent movement of the intermediate member from a cocked position.

7. An autoinjector according to claim 6, wherein the trigger arrangement includes a latch member (48) engageable with an abutment surface (46) on the plunger (42), and releasable by a trigger button (38).

8. An autoinjector according to claim 7, wherein the rearward end of said first spring acts on the trigger button to bias it away from the release position.

9. An autoinjector for receiving in use a syringe containing a dose of medicament, said syringe (12) comprising a syringe body (14) of generally cylindrical form, a needle (18) at the forward end of the syringe body, and a piston (20) slideably mounted in said syringe body for expressing a dose,
    said autoinjector comprising:
        a housing (10) for receiving in use said syringe (12) for sliding movement between a retracted position and an extended, injection position in which said needle (18) projects from said housing;
        a drive mechanism (30-36) for being released from an energised condition to drive the syringe forwards to the injection position and to expel a dose;
    wherein said drive mechanism includes:
        a plunger (36) adapted to drive said piston (20) in use;
        an intermediate drive member (34);
        a first compression drive spring (30) disposed between said intermediate drive member and said housing or a part associated therewith to urge said intermediate drive member forwardly (34), and
        a second compression spring (32) acting between said intermediate drive member and said plunger to urge said plunger (36) forwardly,
    wherein immediately on release of said drive mechanism said intermediate drive member (34) and said plunger (34) are freed for relative movement.

10. An autoinjector for receiving in use a syringe containing a dose of medicament, said syringe (12) comprising a syringe body (14) of generally cylindrical form, a needle (18) at the forward end of the syringe body, and a piston (20) slideably mounted in said syringe body for expressing a dose,
    said autoinjector comprising:
        a housing (10) for receiving in use said syringe (12) for sliding movement between a retracted position and an extended, injection position in which said needle (18) projects from said housing;
        a drive mechanism (30-36) for being released from an energised condition to drive the syringe forwards to the injection position and to expel a dose;
    wherein said drive mechanism includes:
        a plunger (36) adapted to drive said piston (20) in use;
        an intermediate drive member (34);
        a first compression drive spring (30) disposed between said intermediate drive member and said housing or a part associated therewith to urge said intermediate drive member forwardly (34), and
        a second compression spring (32) acting between said intermediate drive member and said plunger to urge said plunger (36) forwardly,
wherein the second spring (34) is selected such that the spring force it exerts when substantially fully compressed is less than the force exerted by the first spring when it is fully expanded the syringe is in its injection position.

11. An autoinjector according to claim 10, wherein upon release of said drive mechanism, said intermediate member (34) and said plunger (36) move as one until the syringe reaches the injection position.

12. An autoinjector for receiving in use a syringe containing a dose of medicament, said syringe (12) comprising a syringe body (14) of generally cylindrical form, a needle (18) at the forward end of the syringe body, and a piston (20) slideably mounted in said syringe body for expressing a dose, said autoinjector comprising:
- a housing (10) for receiving in use said syringe (12) for sliding movement between a retracted position and an extended, injection position in which said needle (18) projects from said housing;
- a drive mechanism (30-36) for being released from an energised condition to drive the syringe forwards to the injection position and to expel a dose;

wherein said drive mechanism includes:
- a plunger (36) adapted to drive said piston (20) in use;
- an intermediate drive member (34);
- a first compression drive spring (30) disposed between said intermediate drive member and said housing or a part associated therewith to urge said intermediate drive member forwardly (34), and
- a second compression spring (32) acting between said intermediate drive member and said plunger to urge said plunger (36) forwardly, wherein, prior to release of said drive mechanism said first compression spring exerts a stronger spring force than said second compression spring.

13. An autoinjector for receiving in use a syringe containing a dose of medicament, said syringe (12) comprising a syringe body (14) of generally cylindrical form, a needle (18) at the forward end of the syringe body, and a piston (20) slideably mounted in said syringe body for expressing a dose, said autoinjector comprising:
- a housing (10) for receiving in use said syringe (12) for sliding movement between a retracted position and an extended, injection position in which said needle (18) projects from said housing;
- a drive mechanism (30-36) for being released from an energised condition to drive the syringe forwards to the injection position and to expel a dose;

wherein said drive mechanism includes:
- a plunger (36) adapted to drive said piston (20) in use;
- an intermediate drive member (34);
- a first compression drive spring (30) disposed between said intermediate drive member and said housing or a part associated therewith to urge said intermediate drive member forwardly (34), and
- a second compression spring (32) acting between said intermediate drive member and said plunger to urge said plunger (36) forwardly, wherein, following release of said drive mechanism, said first compression spring expands to urge said intermediate member forward to drive in use said syringe to its injection position.

14. An autoinjector according to claim 13, wherein during the initial expansion movement of said first compression spring, said intermediate member transmits motion to said syringe via said at least partially compressed second spring and said plunger whilst said plunger remains stationary relative to the syringe and towards the end of the expansion of said first compression spring, said syringe is arrested at its injection position, whereupon continued expansion of said first spring compression spring urges said plunger forwardly relative to the syringe to commence expulsion of the dose, and thereafter said second compression spring expands to complete the expulsion of the dose.

15. An autoinjector according to claim 14, wherein at or near the end of the expansion of said first compression spring, said intermediate member moves into engagement with said syringe.

16. An autoinjector according to claim 15, wherein there is little or no expansion of said second spring before the first spring has fully expanded.

17. An autoinjector according to claim 2, wherein upon release of said drive mechanism, said intermediate member (34) is urged close to or in contact with the rear end of the syringe, thereby substantially completely to enclose the second spring to constrain it externally.

* * * * *